United States Patent [19]

Hess et al.

[11] Patent Number: 5,430,175
[45] Date of Patent: Jul. 4, 1995

[54] CAGED CARBOXYL COMPOUNDS AND USE THEREOF

[75] Inventors: George P. Hess, Ithaca; Barry K. Carpenter, Slaterville Springs, both of N.Y.; Doraiswamy Ramesh, San Diego, Calif.; Raymond Wieboldt, Freeville, N.Y.

[73] Assignee: Cornell Research Foundation, Inc., Ithaca, N.Y.

[21] Appl. No.: 159,190

[22] Filed: Nov. 30, 1993

[51] Int. Cl.$^6$ ............................................. C07C 69/00
[52] U.S. Cl. ................................. 560/130; 560/156; 560/144
[58] Field of Search .................... 500/130, 144, 156

[56] References Cited

U.S. PATENT DOCUMENTS 4,981,985  1/1991  Kaplan et al. ..................... 556/50
5,252,743 10/1993  Barrett et al. ................... 548/303.7

*Primary Examiner*—Arthur C. Prescott
*Attorney, Agent, or Firm*—Bruce Jacobs

[57] ABSTRACT

Caged carboxyl compounds in which a 2-alkoxy-5-nitrophenyl photosensitive group blocks a carboxyl function are disclosed. Preferably the compounds are neuroactive amino acids. The compounds are photolyzable by laser pulses at wavelengths above about nm within about 3 μs and provide a product quantum yield of greater than about 0.2.

6 Claims, 4 Drawing Sheets

CAGED CARBOXYL COMPOUNDS AND USE THEREOF

U.S. GOVERNMENT RIGHTS

The U.S. government has rights in this invention in view of N.I.H. grants GM04842 and RR04804 and N.I.H. training grant T32 GM08267-04.

BACKGROUND OF THE INVENTION

Caged compounds are artificial molecules whose biological activity is controlled by light, usually by photolytic conversion from an inactive to an active form. The term "caged" has become popular because it is brief and pictorial, not because it is accurate. In nearly all useful caged biological molecules to date, simple covalent bond formation masks some feature important for biological recognition. Photochemical cleavage of that single bond releases the active species.

Caged compounds are biologically useful because illumination can be easily controlled in timing, location, and amplitude. Therefore abrupt or localized changes in concentration of active species can be generated with controlled amplitudes. This capability is particularly valuable when rapid mechanical mixing is impractical, for example, on the surface of or inside a more-or-less intact cell, tissue, or protein crystal, or when microscopic spatial gradients are desired. Photolysis of caged compounds is one of the best techniques to examine the fast kinetics or spatial heterogenity of biochemical responses in such systems.

Caged compounds are most commonly designed by modifying a desired biomolecule with a suitable photoremovable protecting or "caging" group. To be useful in biological experiments, the protecting group must satisfy several requirements, at least partially. First, it should render the biomolecule inert to the biological system used. Second, it should release the biomolecule in high yield at sufficient speed by photolysis at wavelengths of light that are non-detrimental to the biological preparation. Third, any photoproducts other than the desired biomolecule should not interact or interfere with the biological system.

Caging groups based on the photoisomerization of 2-nitrobenzyl (ortho-nitro-benzyl) derivatives are the most prevalent in present caged compounds. However, its usein biological systems has been limited because the photoproduct, 2-nitrosobenzaldlehyde, may react with the released compound or other components of the preparation. Nevertheless, it has been tested for derivatives of ATP, inositol polyphosphate, calcium chelators, amino acids and proton chelators.

A recent review of caged compounds and identification of many caging groups is "Controlling Cell Chemistry with Caged Compounds", Adams et. al., *Annu. Rev. Physiol*, 1993 55:755–84. Numerous other photolabile caging compounds have been reported in the literature, including benzyl bromides; 1-($\alpha$-diazobenzyl)pyrene; N-hydroxy-2-thiopyridone; N-hydroxysuccinimidyl p-azidobenzoate; N-hydroxysuccinimidyl ester of p-azidobenzoylglycine; N-hydroxysuccinimidyl pbenzoylbenzoate; p-pentachlorophenyl ester of p-benzoylbenzoylglycine; (bromomethyl)phenylacetate; 1-peptidyl-5-bromo-7-nitroindoline; as well as aromatic diazo compounds such as 1-(2-nitro-4,5-dimethoxy)phenyl-diazoethane, 1-(2-nitro)phenyl-diazoe 2-nitro-3,4,5,6-tetramethyl-diazoethane.

Caged compounds have been used recently in chemical kinetic investigations of neurotransmitterreceptors. Hess, Determination of the Chemical Mechanism of Neurotransmitter Receptor-Mediated Reactions by Rapid Chemical Kinetic Techniques, Biochemistry, 32:989-1000 (1993). Rapid mixing iS an experimenteL1 problem in investigations of these receptors, which are proteins embedded in the membrane of muscle and nerve cells. The proteins control the transmission of signals between cells of the nervous system, and are implicated in a wide variety of diseases and thus are the targets of many clinically important drugs. Some steps of the receptor-mediated reactions involve the binding of a neurotransmitter to its constituent receptor and the opening of transmembrane channels, and occur in less than a millisecond. Determination of the chemical mechanism of the reactions, which must be investigated in intact cells in the sub-ms time region, has been a central goal in neurobiology for several decades. Recently, chemical kinetic investigations of neurotransmitter receptors in intact $BC_3H1$ cells in the $\mu s$ time region were reported.

The introduction of the $\alpha$-carboxy-o-nitrobenzyl group for protecting carbamate amino groups allowed the synthesis of caged carbamoylcholine. (Milburn et. al., Biochemistry 28:48–55 (1989)) This compound is biologically inert, but can be photolyzed to carbamoylcholine, a well-characterized analogue of acetylcholine, with a $t_\frac{1}{2}$ of 40 $\lambda s$. Thus, it became possible to equilibrate receptors on a cell surface with caged carbamoylcholine, liberate carbamoylcholine by a laser pulse within about 120 $\lambda s$, and investigate the kinetics of the formation of acetylcholine receptorchannels on a $\lambda s$ time scale. HoweVer, photolysis of analogous Ncaged derivatives of gamma-aminobutyric acid (GABA) and glycine which activate specific inhibitory receptors in the central nervous system occurs in the ms time region and with low product quantum yield (<0.05).

Kuzmic et. al., Collect. Czech. Chem. Commun., 51:1293–1300 (1986) contains a report of the photochemical hydrolysis of a series of nitrophenyl acetates.

The desire to make chemical kinetic measurements in the $\lambda s$-toms time region with receptors for these central nervous system neurotransmitters required more suitable caged compounds and is an object of this invention.

In particular, it is an object of this invention to produce a photosensitive blocking group for the carboxyl function of amino acids, e.g. glycine, aspartic acid, beta-alanine and $\mu$-aminobutyric acid (GABA), and the excitatory neurotransmitters, e.g. glutamic acid and N-methyl-D-aspartic acid (1VMDA).

SUMMARY OF THE INVENTION

The present invention is directed to novel compounds wherein the carboxylic functionality is caged, new caging groups, and the use of the caged compounds to rapidly photolyze and deliver a neurotransmitter to a desired site.

More specifically, this invention is directed to novel caged carboxylic acids containing a 2-alkoxy-5-nitrophenyl protecting group. The caged compounds photolyZe within about 5 $\lambda s$ and provide a quantum yield in an amount greater than 0.15.

The caged carboxylic acid has a general formula:

Q-COO-R wherein Q-COO- is a carboxyl-containing organic moiety and R is 2-alkoxy-5-nitrophenyl wherein the alkoxy group contains abo carbon atoms. Preferably Q-COO- is an amino acid. Most preferably the amino acid is a neuroactive amino acid. Also preferably R has 1 carbon atom, i.e. is methoxy.

The present invention furtherirelates to the use of the novel caged compound to release the underlying carboxylic acid by photolysis of the protecting 2-alkoxy-5-nitrophenyl group, by exposing the caged compound to light at a wavelength of greater than about 300 nm for a period of less than about 10 λs.

DETAILED DESCRIPTION OF THE INVENTION

The present invention comprises caged compounds having the general formula:

Q-COO-R wherein Q-COO- is derived from a carboxyl-containing organic compound, preferably from an amino acid, most preferably from a neuroactive amino acid, and R is 2-alkoxy-5-nitrophenyl wherein the alkoxy group contains about 1-4 carbon atoms. Preferably the alkoxy group is methoxy.

Specific examples of such compounds include 2-methoxy-5-nitrophenyl glycine ester, 2-ethoxy-5-nitrophenyl glycine ester, 2-pro-poxy-5-nitrophenyl glycine ester, 2-butoxy-5-nitrophenyl glycine ester, 2-methoxy-5-nitrophenyl β-alanine ester, 2-methoxy-5-nitrophenyl asparagine ester, 2-methoXy-5-nitrophenyl-Y-aminobutyric acid ester. A representative listof additional neuroactive amino acids which can be protected by the 2-alkoxy-5-nitrophenyl group includes: saclofen; S-sulpho-L-cysteine; Y-N-oxalyl-L-α,Y-diaminobutyric acid; 0-phospho-D-serine; philanthotoxin 343, (±)-cis-2,3piperidinedicarboxylic acid; piperidine-4-sulphonic acid; L-trans-pyrrolidine-2,4-dicarboxylicacid;isoguvacine;indole-2-carboxYlic acid; kalnic acid mono-methyl ester; (+)-α-methyl-4-carboxyphenylglycine; 6-nitroquinoxaline-2,3-dione; Y-D-glutamylaminoethylphosphonic acid; D-homocysteic acid; L-homocysteinesulphinic acid; (RS)-3-Hydroxyphenylglycine; 3-hydroxy-2-quinoxaline-carboxylic acid; 5-7-dichlorokynurenic acid; dihydrokainic acid; domoic acid; L-glutamic acid; (S)-4-carboxyphenylglycine; 6.-chlorokynurenic acid; D-cysteic acid; L-cysteine sulphinic acid; (±)-3-Carboxyphenylalanine; (R)-5-bromowillardiine; aminomalonic acid; and many others. Each of these compounds aswell as all other neuroactive amino acids contain carboxylic acid groups (-COOH) that can be protected by the 2-alkoxy-5-nitropheny! protecting group in accordance with this invention.

Other suitable protectable compounds with a carboxyl group which are useful in the present invention are identified in Gilman, A.G. et. al., *The Pharmacological basis of Therapeutics* (8th ed.) Macmillan, New York (1990). Moreover, peptides may also be protected. Peptides, like proteins that are involved. in all biological reactions and form important structural components of all organisms, also contain protectable carboxyl groups. Suitable such peptides are disclosed in one or more of the following articles: M. Patek, Multistep Deprotection for Peptide Chemistry (1993) Int. J. Pept. Protein Res. 42, 97–117; G. Jung et. al., Multiple Peptide Synthesis Methods and their Applications (1992) Angew. Chem. Int. Ed. Engl. 31, 367–383; T.W. Muir et. al., The Chemical Synthesis of Proteins (1993) Curr. Opin. Biotechnol. 4,420–427; P.D. Gesellchen et. al., Synthesis of Peptides and Proteins by Chemical and Biotechnological Means, in Advances in Parenteral Sciences, Vol 4., V. H. L. Lee, ed., Marcel Dekker, Inc., New York, 1991, p. 57–135; J.P. Tam et. al., Strong Acid Deprotection of Synthetic Peptides: Mechanisms and Methods, in Peptides: Analysis, Synthesis, Biology, Vol. 9, Special Methods in Peptide Synthesis, part C, s. Udenfriend et al. eds., Academic Press, Inc., San Diego, 1987, p. 185–248.

The caged compounds are prepared by means of an esterification reaction, i.e. by reacting a carboxylic acid with a 2-alkoxy-5-nitrophenol, generally in the presence of one or more esterification catalysts under conventional esterification reaction conditions. Since functionalities other than carboxyl also react with phenols, if such other functionality is present on the carboxylic acid then it must be blocked prior to the phenol reaction. Thus for the amino acid glycine, N-butyloxycarbonylglycine in which the amino group is blocked by the butyloxycarbonyl group (BOC), is conveniently used. Other acid labile blocking groups for amino groups are benzyloxycarbonyl, p-methoxy benzyloxycarbonyl, triphenylmethyl, o-nitrobenzene sulfonyl, and toluene sulfonyl. Still further blocking groups can be found in the literature, including such as Bodanszky et. al., *The Practice of Peptide Synthesis*, Springer Verlag (1984).

Catalysts suitable for use herein include the conventional esterification catalysts which are well known. A particularly good catalyst system for forming glycine esters is the combination of Nhydroxybenzotriazole and 4-dimethylaminopyridine. Additional suitable catalysts include such as N-hydroxysuccinimide, 2-(5-norbornene-2,3-dicarboximido)-1,1,3,3-tetramethyluronium-tetrafluo and N-hydroxy-5-norbornene-endo-2,3,-dicarboximide.

To facililitate the esterification reaction the use of a coupling agent such as 1-(3-dimethylaminopropyl)-3-ethyl carbodiimide hydrochloride is recommended. Alternative suitable coupling agents include such as N,N-dicyclohexylcarbodiimide, benzotriazole-1-yloxy-tris-(dimethylamino)-phosphonium hexafluorophosphate, 2-(1H-benzotriazole-1-yl)-1,1,3,3-tetramethyluronium hexafluorophosphate, and bromo-tris-pyrrolidino-phosphonium hexafluorophosphate.

The reaction will generally be performed in the presence of a solvent. Suitable such solvents include methylene chloride, dimethylformamide, dry ether, tetrahydrofuran, ethyl acetate, toluene:chloroform 1:1.

The reaction should be run under conditions which will minimize potential side reactions, especially when the reactants are initially mixed. A good way to accomplish this has been found to be the use of low temperatures, i.e. below about −50° C., preferably at about −78° C. The initially cold mixture is allowed to warm slowly while the overall coupling procedes to completion. Alternatively the reaction may be moderated by slowly adding the reactants without allowing the temperature to increase above about 30° C.

If the caged compound contains blocked functional groups for non-carboxyl functionality, then those groups, e.g.. BOC for amines, will need to be removed without disturbing the 2-alkoxy-5-nitrophenyl carboxyl cage group. Techniques for so doing are well known in the literature for other blocking groups and should function in like manner. A particularly good technique for removing BOC from caged glycine entails the use of a combination of anhydrous ethyl acetate and hydrogen chloride. Other suitable techniques include trifluoro acetic acid hydrolysis, catalytic hydrogenation, deprotection with hydrogen fluoride, or hydrobromic acid in acetic acid or in trifluoroacetic acid.

The 2-alkoxy-5-nitrophenyl caging groups are useful in the synthesis and characterization of photolabile precursors of neurotransmitters and as well as other compounds that contain carboxyl groups, and for kinetic investigations of neurotransmitter receptors in central nervous system cells in the microsecond time domain.

As shown in the examples below, the 2-methoxy-5-nitrophenyl caging group for the carboxyl function of glycine produced a caged glycine compound which was photolyzed within 3 μs with a product quantum yield of 0.2. In comparison, the best previously available caged glycine derivative, N-(α-carboxy-2-nitrobenzyl)glycine (Billington et al, Biochemistry, 31:5500–507 (1992)), was photolyzed with a time constant τ of 1.6 ms at pH 7.5 and a product quantum yield of only 0.02.

In the non-limiting Examples below, all parts and percents are by weight unless otherwise stated.

EXAMPLE i

Preparation of 2-Methoxy-5-Nitrophenyl Glycine

Preparation of N-BOC-(2-methoxy-5-nitrophenyl) Glycine Ester

To a mixture of N-butyloxycarbonylglycine (193 mg, 1.1 mmol), 2-methoxy-5-nitrophenol (170 mg, 1 mmol), N-hydroxybenzotriazole (10 mg, 0.075 mmol), 4-dimethylaminopyridine (10 mg, 0.08 mmol) and 1-(3-dimethylaminopropyl)-3-ethyl carbodiimide hydrochloride (230 mg, 1.2 mmol) stirred at −78° C., methylene chloride (7 ml) was added by syringe. The reaction was continued overnight and the temperature was allowed to rise to room temperature. The methylene chloride solution was washed with water (2×5 ml),, aq. NaHCO$_3$ (5%, 3×5 ml), water (2×5 ml), aq. citric acid (10%, 3×5 ml) and brine (1×3 ml), and dried over anhydrous MgSO$_4$. Column chromatography on TLC silica gel using hexane and ether eluent gave the product as a colorless solid. Yield: 200 mg (75%); mp: 121°–122° C. $^1$H-NMR (CDC13): 8.16 (dd, J=9.1 and 2.7, 1H, C$_4$-H); 7.98 (d, J=2.6, 1H, C$_6$-H); 7.0 (d, J =9.1, 1H, C$_3$-H); 5.06 (bs, 1H, -NHCO$_2$); 4.21 (d, J=5.7, 2H, CH$_2$NHCO$_2$); 3.91 (s, 3H, OCH$_3$) and 1.45 (s, 9H, CO$_2$C(CH$_3$)$_3$). C,H,N analysis calculated for C$_{14}$H$_{18}$N$_2$O$_7$: 51.13 (C%), 5.52 (H%) and 8.59 (N%); found: 51.32 (C%), 5.41 (H%) and 8.53 (N%).

REMOVAL OF BOC GROUP

A solution of N-BOC-(2-methoXy-5-nitrophenyl) glycine ester (45 mg, 0.14 mmol) in anhydrous ethylacetate (saturated with HCl gas) at −78° C. was stirred overnight and allowed to reach room temperature. The precipitated solid was filtered, washed with ethylacetate and dried. Yield: 35 mg (96%); mp: 185°–188° C. (dec). C,H,N analysis calculated for C$_9$H$_{11}$N$_2$O$_5$C: 41.06%(C), 4.18%(H) and 10.65%(N); found: 41.10%(C), 4.34%(H) and 10.44%(N).

EXAMPLE II

Figure 2:
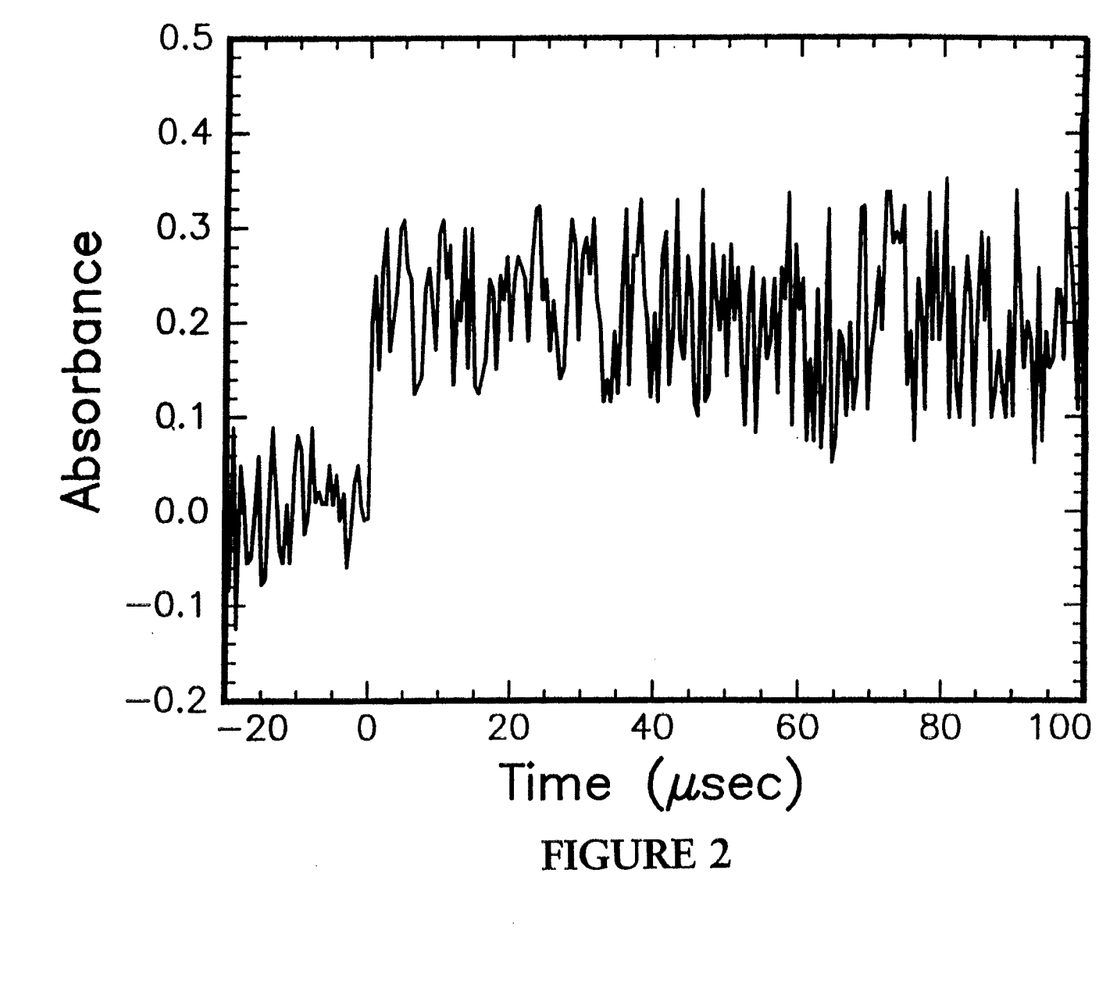
FIG. 2 is a trace of the photolysis of 2-methoxy-5-nitro-phenylglycine

To evaluate the photolysis characteristics of the 2-methoxy-5-nitro glycine ester of Example I, laser pulse photolysis was performed and the results thereof are shown in FIG. 2 by the rapid absorbance jump produced by the photolysis of the ester. The light source used to initiate the photolysis reaction was a Lumonics TE861M excimer laser. The lasing medium was either 2% N$_2$ in helium, which produced a primary energy of 6 mJ at 337 nm with a 4 ns pulse width, or a XeCl mix that produced 70 mJ at 308 nm in 6 ns pulses. For cell photolysis, the ×7 nm light was delivered to the microscope stage for use in whole-cell recording measurements with a 300 μm core optical fiber (FiberGuide Industries); 10% of the primary energy was typically coupled through the fiber to the cell preparation. Rapid absorbance changes of caged compound solutions were measured with a transient absorbance spectrophotometer in which 308 nm light from the primary output of the laser was focussed into a 2×2 mm quartz cuvet and the absorbance changes produced were monitored at right angles to the laser beam with a single beam transient spectrophotometer whose signal transfer parameters effectively produced 500 kHz filtering of the rapid absorbance jump. The photocurrent Was amplified with a Thorn EMI model A1 preamplifier, which also acted as a low ]pass filter with cutoff dependent on the amplification selected; the cutoff frequencies were between 50 KHz and 50MHz. The rapid absorbance jump produced in the caged ester solution by single laser flashes could be digitized at up to 2 MHz with a digital oscilloscope and in each case the preamplifier filtering was matched to the digitization rate of the data collection. MeasUrements of the pulsed UV light energy for quantum yield determinations were made with a Gentec ED-200 calibrated thermopile.

The rapid jump in absorbance at 380 nm following laser-pulse photolysis of the caged glycine indicated that the conversion to products and, therefore, the release of free glycine, occurred on a μs time scale. Absorbance measurements of the fast jump were made over the range 350 to 450 nm and the resulting profile matched the absorbance spectrum of the expected 2-methoxy-5-nitrophenol. Measurements of triplet quenching in the reaction of 2-methoxy-5nitrophenyl acetate by Kuzmic et al. (supra) indicate that the lifetime of the photohydrolysis reaction is 0.15 μs. The maximum time resolution of the transient absorbance measurements in our study is 0.5 μs. However, within the limits of the data collection instrumentation used here, the absorbance change at 380 nm appears as a step jump indicating that the conversion to products occurs within 3 μs. The photolysis was also performed with the 337 nm light source from the excimer laser and produced a jump in absorbance that was as fast as the one induced by 308 nm light. The 6mJ of energy available at the 337 nm wavelength produced a smaller absorbance change than the one shown in FIG. 2.

The product quantum yield from photolysis of the caged glycine was estimated by comparison to the photolysis of 2-methoxy-5-nitrophenyl acetate, which was used as an actinometric standard. A quantum yield of 0.22 was found for a 1 mMsolution of 2-methoxy-5nitrophenyl acetate in 100 mMphosphate buffer at pH 7.0 that also contained 20% acetonitrile to substituted for caged glycine.

EXAMPLE III

A 1.1 mM solution of the caged glycine of Example I was prepared in extracellular recording buffer at pH 7.1. The hydrolysis reaction was followed spectrophotometricallY in a 0.2 cm cuvette and the results shown in FIG. 1 which demonstrate that the hydrolysis led to glycine and 2-methoxy-5+nitrophenol. The caged glycine ester was rapidly dissolved in buffers to produce approximately 800 µM solutions of the caged compound and immediately transferred to a 2×2 cuvette in a Hewlett Packard model 8452A diode array spectrophotometer set up to collect spectra at timed intervals. The initial rates of the hydrolysis reaction were obtained from absorbance measurements at 310, 360 and 384 nm after subtraction of the absorbance of the completely hydrolyzed solutj. on. The spectra of the fully hydrolyzed solutions iwere identical in all cases to reference spectra of 2-methoxy-5-nitrophenol at the different pH values. The upper trace at 310 nm represents the spectrum of the compound before hydrolysis. The lower trace at 310 nm corresponds to the fully hydrolyzed material and matches the spectrum of 2-methoxy-5-nitrophenol at pH 7.0. The spectra were acquired at 1, 2, 3, 4, 6, 8, 11 and 60 min after the initial rapid dissolution in buffer. All measurements were performed at room temperature (22°-24° C.) .

Figure 1:
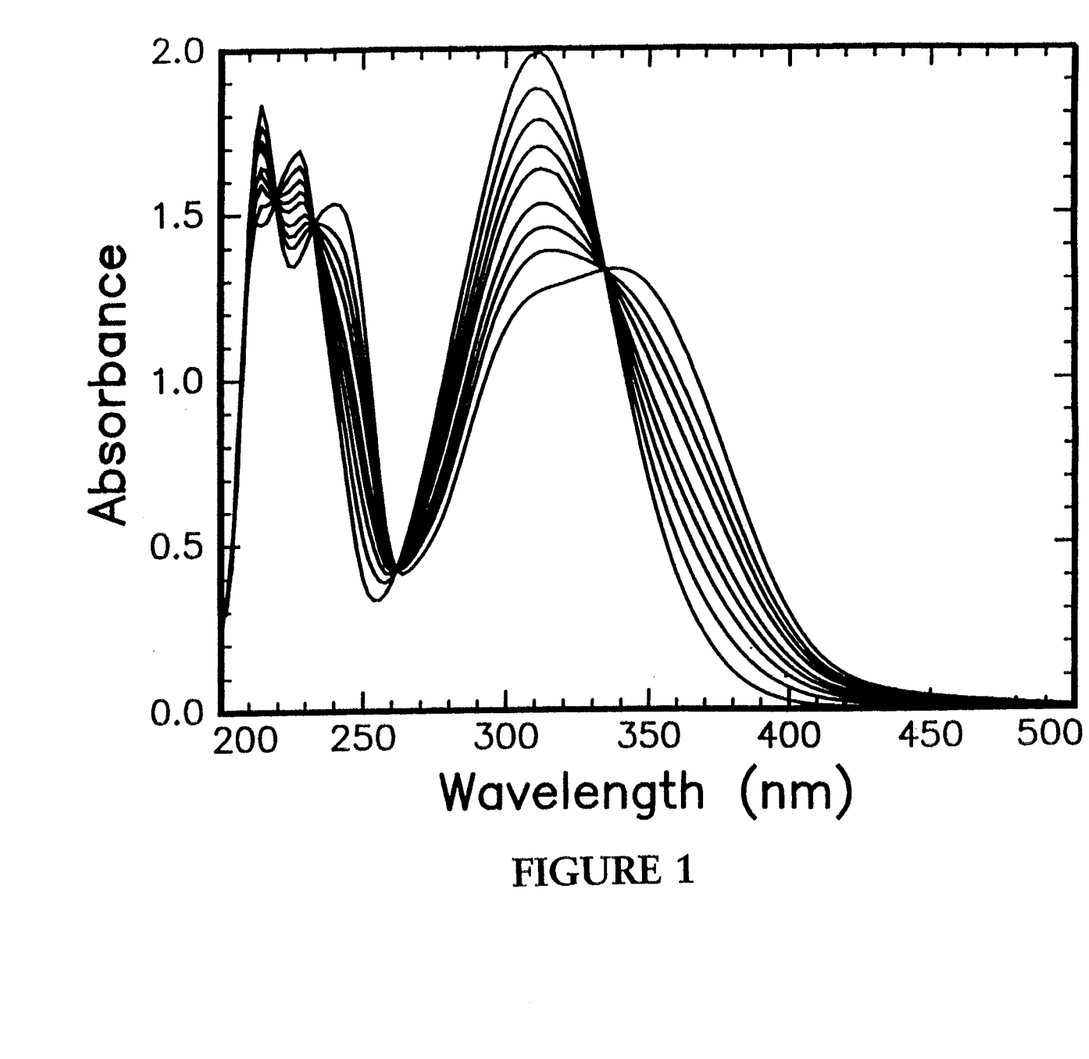
FIG. 1 is a spectrum of 2-methoxy-5-nitrophenylglycine (caged glycine) of Example I and its hydrolysis products.

FIG. 1 shows that the caged glycine hydrolyzed spontaneously at neutral pH in Hepes buffered solution used for whole-cell recording. The decay of the absorbance signal at 310 nm is closely fitted by a single exponential function with a time. constant of 6.1 min.

2-Methoxy-5-nitrophenyl glycine ester is hydrolyzed in water at pH 7.1 with a time constant of 6.1 min. The compound is, however, quite stable at pH 4.0 ( for hydrolysis is about 3 hr). The hydrolysis result may involve intramolecular ]participation of the amino group but there may be other factors involved as well. The slow hydrolysis of the caged glycine at pH 7.1, however, poses no problem in kinetic investigations of a glycine receptor. The caged compound can be kept at pH 4.0 before use in kinetic experiments in which the solution is rapidly shifted to physiological pH.

EXAMPLE IV

Whole-cell current recording was performed as follows. The preparation of embryonic mouse cortical cells was as described by Geetha et al. (Biochemistry 31:5488-5499 (1992)). The extracellular recording buffer was 145 mM NaCl, 1.8 MMMgCl$_2$, 1 mM CaCl2 and 10mMHepes (pH 7.4) and the intracellular buffer was 145 mM CsCl, 1mM CaCl$_2$, 10 mM EGTA [ethyleneglycol-bis-(beta-aminoethYl ether) N,N,N'N,-tetraacetic acid]and 10 mM Hepes (pH 7.2). The flow method used to equilibrate receptors on the surface of a single cell with ligands within 10 ms has been described by Udgaonkar et al (Proc. Natl, Acad. Sci. USA, 84:8758-8762 (1987)). The whole-cell current responses were determined in mouse cortical neurons, pH 7.1, −40 MV, room temperature (22° C) . Caged glycine solutions at pH 4.0 in extracellular buffer but containing only 5 mM Hepes were mixed in 1:1 proportions with iextracellular recording buffer containing 20 mM Hepes at pH 7.4 using a low volume T-tube mixer before the solutions entered the U-tube that delivered the solution stream at pH 7.1 to the cell at a linear flow rate of 0.5 cm s$^{-1}$. The whole-cell current due to opening of glycine receptor channels was recorded using the technique of Hamill et. al. (Pflugers Arch, 391:85-100 (1981)). All other details of the cell-flow technique, and the combination of the cell-flow technique with the laser-pulse photolysis technique in which the whole-cell current is measured after photolysis of caged neurotransmitter, were as described by Matsubara et al (Biochemistry, 31:5507-5514 (1992)). Hydrolysis of the caged glycine before it was applied to a cell was prevented by the mixer strategy.

Figure 3:
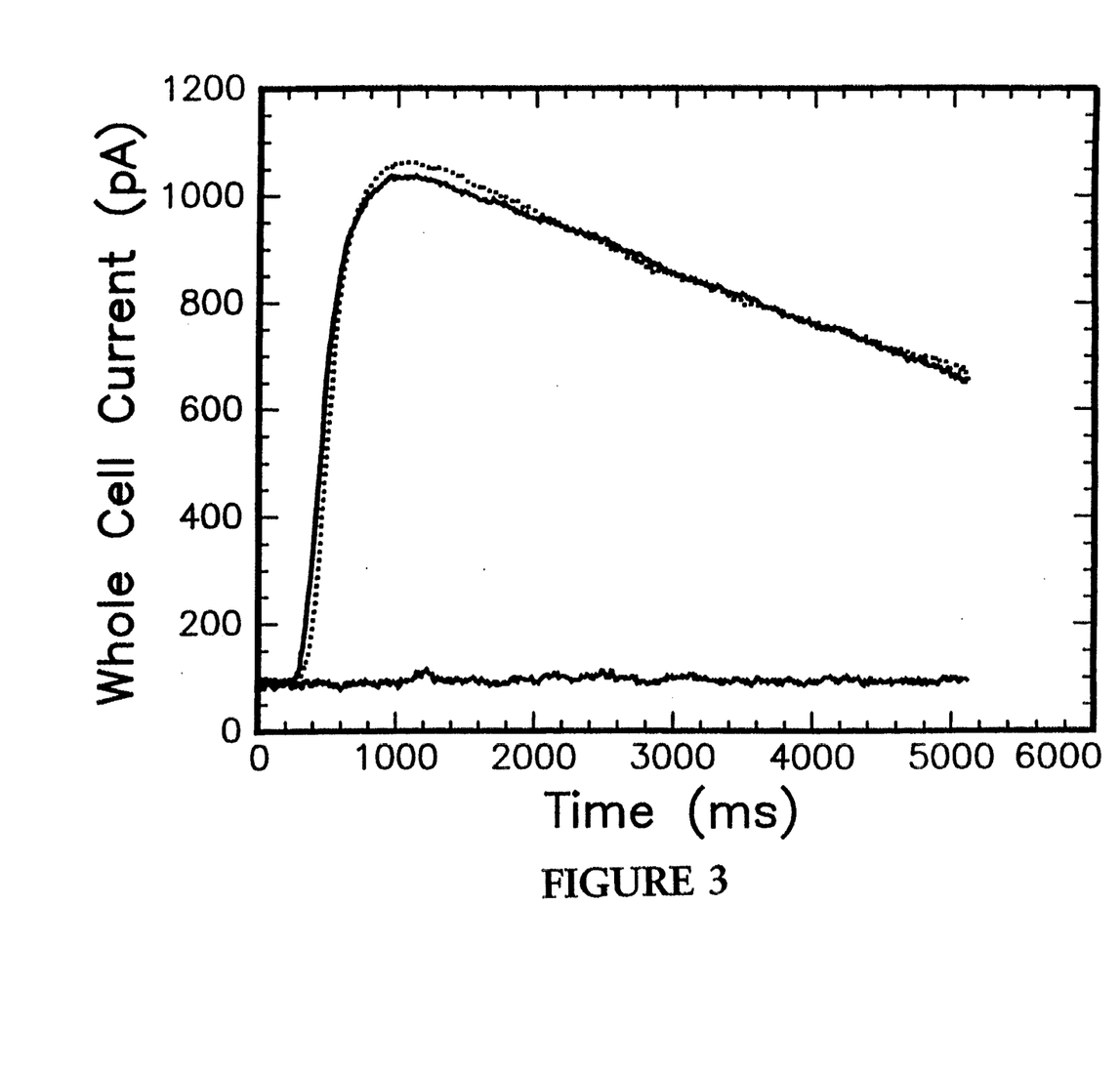
FIG. 3 is a trace of the whole cell current responses determined in mouse cortical neurons. at pH 7.1, −40mV, and at room temperature.

FIG. 3 shows that the caged glycine does not interfere with activation of cell currents from glycine receptor channels in mouse cortical neurons. Specifically, the caged glycine solution with and without free glycine at pH 4.0 was rapidly mixed with extracellular buffer to produce a solution of pH 7.1 before flowing it over the cell. A control solution of 85 µM free glycine (170 M glycine in extracellular buffer mixed with pH 4 buffer used to stabilize the ester) is shown by the solid trace in FIG. 3. An identical response was produced when 170 µM glycine in extracellular buffer was mixed with 1.1mMcaged glycine ester in pH 4 buffer as shown by the dotted line trace. Caged glycine at pH 4.0 mixed with external buffer did not activate any whole cell current, as shown by the lower trace at the baseline current. There was no observable inhibition or activation by caged glycine. Calibration of the mixer was performed to show that solutions were delivered at equal rates from both supply lines. Identical current responses were obtained when 170 µM glycine in pH 7.4 buffer was mixed with pH 4 buffer when the solutions were alternately applied from the two different supply lines of the mixer (data not shown).

Figure 4:
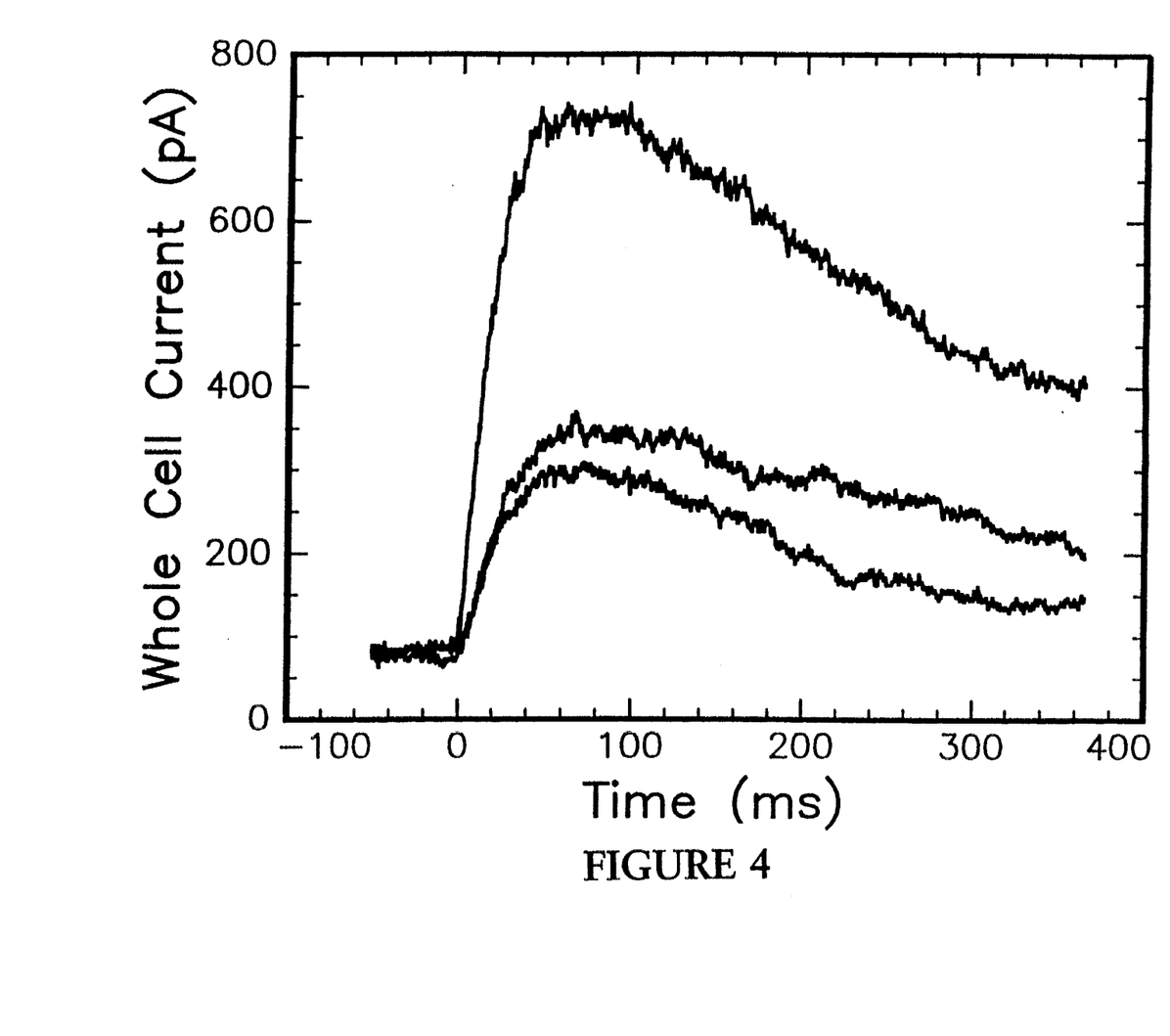
FIG. 4 is a trace of the whole cell current produced by photolysis of 2-methoxy-5-nitrophenylglycine.

Furthermore, FIG. 4 indicates that the cell-flow laser-pulse photolysis technique, together with the new caged glycine derivative, is useful to investigate the chemical mechanism of the glycine receptor. Three phases of the reaction can be observed in one and the same experiment. First, the current rise time is well-fitted by a single exponential for over 90% of the reaction, suggesting that what is observed is a single step of the channel-opening process. At low glycine concentrations this rising phase is expected to reflect the rate constants for the ligand-binding steps. At high ligand concentrations, when the opening of the channel becomes rate limiting, the rate constants for channel opening can be determined. Second, the current amplitude is a measure of the concentration of open receptor channels before the receptor desensitizes. The effect of glycine concentration on the amplitude can be used to determine the dissociation constant of the receptor:ligand complexes and the equilibrium constant for channel opening. Finally, the falling phase of the current provides information about receptor desensitization.

In FIG. 4, the whole-cell current produced by photolysis of the caged glycine is shown. Specifically, a 1.4. mM solution of caged glycine, prepared in external cell buffer that was weakly buffered at pH 4, was rapidly combined with pH 7.4 cell buffer in the mixer to produce 700 μM caged compound at a final pH of 7.1. The cell was exposed to this solution for 700 ms before photolysis was initiated by a laser pulse at time 0. The preincubation baseline was a sensitive indicator of free glycine in the final mixture. In practice, frozen aliquots of freshly prepared caged glycine pH 4 solution were thawed before application with the mixer and could be used for up to 20 min without detectable glycine currents appearing in the preincubation baseline:. The yield of free glycine was reproducibly varied by adjusting the energy of the laser pulse; the free glycine concentration was calibrated by comparison of the maximum current produced by photolysis with the current from a control 75 μM glycine solution in external buffer flowed over the cell. The rising phase of the current is fitted well by a single exponential model for all three concentrations produced by photolysis. The upper trace has a rate of 54 s-1 and corresponds to 35 M free glycine, the middle awe a rate of 40 s$^{-1}$ at 18 μMglycine, and the lowest trace a rate of 42 s$^{-1}$ rate at 10 μmglycine. The concentration of released glycine is also affected by the initial concentration of caged glycine, the distance of the cell from the fiber (1 mm in the experiment shown), and the laser pulse energy used (250 to 600 μJ).

2-Methoxy-5-nitrophenyl glycine ester is photolyzed by a laser pulse at 308 or 337 nm within 3 microseconds and. with a product quantum yield of 0.2. The compound is hydrolyzed in water with a time constant T of 6.1 minutes at pH 7.1 and 3 hours at pH 4.0. Mouse cerebral cortical neurons containing glycine receptors were used in biological assays. A cell-flow device, in which solutions of caged glycine at pH 4.0 were mixed with buffer to give a final pH of 7.1, was used to equilibratethe compound with receptors on the cell surface. Neither the caged compound nor the 2-methoxy-5nitrophenol photolysis product affected the glycine receptors or modified their response to glycine. When cells equilibrated with caged glycine were irradiated by a laser pulse at 337 nm, glycine receptor channels were opened, as detected in whole-cell current recordings.

What is claimed is:

1. A photolabile caged carboxylic acid compound of the formula:

Q-COO-R wherein Q-COO- represents an organic moiety derived from a carboxylic acid and R is 2-alkoxy-5-nitrophenyl wherein the alkoxy group contains about 1–4 carbon atoms.

2. The compound of claim 1, wherein Q-COO- is derived from an amino acid.

3. The compound of claim 2, wherein the amino acid is neuroactive.

4. The compound of claim 3, wherein the neuroactive amino acid is selected from the group consisting of aspartic acid; gamma-aminobutyric acid; beta alanine; saclofen; S-sulpho-L-cysteine; Y-N-oxalyl-L-α, Y-diaminobutyric acid; O-phospho-D-serine; philanthotoxin 343, (±)-cis-2,3-piperidinedicarboxylic acid; piperidine-4sulphonic acid; L-trans-pyrrolidine-2,4-dicarboxylic acid; isoguvacine; indole-2-carboxylic acid; alkalnic acid mono-methyl ester; (+)-α-methyl-4-carboxyphenylglycine;6-nitroquinoxaline-2,3-dione; Y-D-glutamylaminoethylphosphonic acid; D-homocysteic acid; L-homocysteinesulphinic acid; (RS)-3-Hydroxyphenylglycine; 3-hydroxy-2-quinoxalinecarboxylic acid; 5-7-dichlorokynurenic acid; dihydroka acid; domoic acid; L-glutamic acid; (S)-4-carboxyphenylglycine; 6-chlorokynurenic acid; D-cysteic acid; L-cysteine sulphinic acid; (±)-3-Carboxyphenylalanine; (R)-5-bromowillardiine; and aminomalonic acid.

5. The compound of claim 1, wherein R is 2-methoxy-5-nitrophenyl.

6. The compound of claim 1 which is 2-methoxy-5-nitrophenyl glycine ester.

* * * * *

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

On the title page item [57],

Line 5: Delete "about nm" and insert --about 300 nm--

Col. 1, l. 48: Delete "usein" and insert --use in--

Col. 2, l. 2: Delete "neurotransmitterreceptors" and insert --neurotransmitter receptors--

Col. 2, l. 6: Delete "iS an experimenteLl" and insert --is an experimental--

Col. 2, l. 29: Delete "$\lambda$s" and insert --$\mu$s--

Col. 2, l. 32: Delete "$\lambda$s" and insert --$\mu$s--

Col. 2, l. 33: Delete "$\lambda$s" and insert --$\mu$s--

Col. 2, l. 34: Delete "HoweVer" and insert --However--

Col. 2, l. 43: Delete "$\lambda$s-toms" and insert --$\mu$s-to-ms--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 2, l. 49: Delete "$\mu$" and insert --$\gamma$--

Col. 2, l. 62: Delete "photolyZe" and insert --photolyze--

Col. 2, l. 62: Delete "$\lambda$s" and insert --$\mu$s--

Col. 3, l. 3: Delete "abo" and insert --about 1-4--

Col. 3, l. 7: Delete "furtherirelates" and insert --further relates--

Col. 3, l. 12: Delete "$\lambda$s" and insert --$\mu$s--

Col. 3, l. 45: Delete "methoXy" and insert --methoxy--

Col. 3, l. 46: Delete "Y-" and insert --$\gamma$--

Col. 3, l. 46: Delete "listof" and insert --list of-

Col. 3, l. 49: Delete "Y-N-oxalyl-L-$\propto$, Y-" and insert --$\gamma$-N-oxalyl-L-$\propto$, $\gamma$--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 3, l. 53:   Delete "carboxYlic" and insert --carboxylic--

Col. 3, l. 55:   Delete "Y-D-" and insert --γ-D---

Col. 3, l. 64:   Delete "aswell" and insert --as well--

Col. 3, l. 67:   Delete "nitropheny!" and insert --nitrophenyl--

Col. 4, l. 6:    Delete "." before "in"

Col. 4, l. 23:   Delete "s." and insert --S.--

Col. 4, l. 47:   Delete "Nhydroxybenzotriazole" and insert --N-hydroxybenzotriazole--

Col. 4, l. 51:   Delete "tetramethyluroniumtetrafluo" and insert --tetramethyluroniumtetrafluoroborate--

Col. 5, l. 41:   Delete "EXAMPLE i" and insert --EXAMPLE I--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 6, l. 3: Delete "methoXy" and insert --methoxy--

Col. 6, l. 9: Delete "$C_9H_{11}N_2O_5C$" and insert --$C_9H_{11}N_2O_5Cl$--

Col. 6, l. 21: Delete "N2" and insert --$N_2$--

Col. 6, l. 36: Delete "kHz" and insert --KHz--

Col. 6, l. 37: Delete "Was" and insert --was--

Col. 6, l. 39: Delete "]pass" and insert --pass--

Col. 6, l. 46: Delete "MeasUrements" and insert --Measurements--

Col. 7, l. 7: Delete "mMsolution" and insert --mM solution--

Col. 7, l. 8: Delete "mMphosphate" and insert --mM phosphate--

Col. 7, l. 16: Delete "spectrophotometricallY" and insert --spectrophotometrically--

UNITED STATES PATENT AND TRADEMARK OFFICE
CERTIFICATE OF CORRECTION

PATENT NO. : 5,430,175  Page 5 of 8

DATED : July 4, 1995

INVENTOR(S) : Hess et al.

It is certified that error appears in the above-indentified patent and that said Letters Patent is hereby corrected as shown below:

Col. 7, l. 18: Delete "2-methoxy-5+nitrophenol" and insert --2-methoxy-5-nitrophenol--

Col. 7, l. 27: Delete "solutj. on." and insert --solution.--

Col. 7, l. 45: Delete "( for" and insert --($\tau$ for--

Col. 7, l. 47: Delete "]participation" and insert --participation--

Col. 7, l. 60: Delete "MMMgCl$_2$" and insert --MM MgCl$_2$--

Col. 7, l. 61: Delete "10mMHepes" and insert --10 mM Hepes--

Col. 7, l. 63: Delete "aminoethYl" and insert --aminoethyl--

Col. 7, l. 63: Delete "N,N,N',N,-" and insert --N,N,N',N',--

Col. 8, l. 5: Delete "iextracellular" and insert --extracellular--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 8, l. 31: Delete "1.1mMcaged" and insert --1.1 mM caged--

Col. 9, l. 9: Delete "baseline:." and insert --baseline.--

Col. 9, l. 18: Delete "35 M" and insert --35 $\mu$M--

Col. 9, l. 19: Delete "$\mu$Mglycine" and insert --$\mu$M glycine--

Col. 9, l. 20: Delete "$\mu$mglycine" and insert --$\mu$m glycine--

Col. 9, l. 27: Delete "and." and insert --and--

Col. 9, l. 34: Delete "equilibratethe" and insert --equilibrate the--

Col. 10, l. 20: Delete "Y-" and insert --$\gamma$-- (two occurrences)

Col. 10, l. 27: Delete "Y-" and insert --$\gamma$--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 8, L 31: Delete "1.1mMcaged" and insert --1.1 mM caged--

Col. 9, L 9: Delete "baseline:." and insert --baseline.--

Col. 9, L 18: Delete "35 M" and insert --35 $\mu$M--

Col. 9, L 19: Delete "$\mu$Mglycine" and insert --$\mu$M glycine--

Col. 9, L 20: Delete "$\mu$mglycine" and insert --$\mu$m glycine--

Col. 9, L 27: Delete "and." and insert --and--

UNITED STATES PATENT AND TRADEMARK OFFICE
CERTIFICATE OF CORRECTION

PATENT NO. : 5,430,175

DATED : July 4, 1995

INVENTOR(S) : Hess et al.

It is certified that error appears in the above-indentified patent and that said Letters Patent is hereby corrected as shown below:

Col. 9, L 34: Delete "equilibratethe" and insert --equilibrate the--

Col. 10, L 20: Delete "Y-" and insert --$\gamma$-- (two occurrences)

Col. 10, L 27: Delete "Y-" and insert --$\gamma$--

Signed and Sealed this

Nineteenth Day of September, 1995

Attest:

BRUCE LEHMAN

Attesting Officer

Commissioner of Patents and Trademarks